United States Patent [19]

Hane

[11] Patent Number: 4,675,595

[45] Date of Patent: Jun. 23, 1987

[54] METHOD FOR MEASURING THE MOISTURE RATIO OF ORGANIC MATERIAL, AND APPARATUS HEREFOR

[75] Inventor: Bengt Hane, Johanneshov, Sweden

[73] Assignee: Stiftesen Institutet for Microvagsteknik, Stockholm, Sweden

[21] Appl. No.: 746,023

[22] Filed: Jun. 18, 1985

[30] Foreign Application Priority Data

Jun. 27, 1984 [SE] Sweden ............................ 8403437

[51] Int. Cl.$^4$ ........................................... G01N 22/04
[52] U.S. Cl. ........................... 324/58.5 B; 324/58.5 R
[58] Field of Search ...................... 324/58.5 R, 58.5 A, 324/58.5 B, 58.5 C, 58 R, 58 C

[56] References Cited

FOREIGN PATENT DOCUMENTS 1116371 9/1984 U.S.S.R. ........................ 324/58.5 A

OTHER PUBLICATIONS

Kraszewski: "An Improved Microwave Method . . .", IEEE Trans. on Industrial Electronics & Control-Nov. 1976-pp. 364-370.
Berliner: "Phase-Sensitive Ultrahigh-Frequency Moisture Gauge"-Ind. Lab. (U.S.A.), vol. 37-No. 10-Oct. 1971.
Jacobsen: "Dainty-Independent Moisture Meter at X-band"-10th European Microwave Conference-Sep. 1980-pp. 216-220.
Kalinski: "Microwave Attenuation Measurements . . . "-Microwave Power Symposium-Jun. 1978-pp. 142-144.
A. Kraszewski-Microwave Aquametry-A Review, 1980, pp. 209-220, Journal of Microwave Power, 15 (4).
Microwave Homodyne Systems by Ray J. King, University of Wisconsin-Published by Peter Peregrims Ltd. on behalf of the Institute of Electrical Engineers, (1978).

Primary Examiner—Reinhard J. Eisenzopf
Assistant Examiner—Jose M. Solis
Attorney, Agent, or Firm—Nies, Webner, Kurz & Bergert

[57] ABSTRACT

A method and apparatus for measuring the thickness corrected moisture ratio of a material, particularly organic material, comprising transmitting microwaves and measuring therewith the damping (A) and phase change (F1) of the microwaves upon their transmission through the material. According to the invention $(W_w/Y)$ is calculated from the expression $A = (W_w/Y) \cdot k_1 + k_3 \cdot t$, where t is the thickness of the material (10) and where $k_1$ and $k_3$ are constants and the term $W_w/Y$ is the weight of the water in the material per unit area. In addition, the term $(W_d/Y)$ is determined from the expression $F1 = (W_w/Y) \cdot k_4 + (W_d/Y) \cdot k_5 + k_6 \cdot t$ in which expression the aforedetermined term $W_w/Y$ is used. The term $W_d/Y$ is the weight of the material in a dry state per unit area and $k_4$, $k_5$, $k_6$ are constants. The moisture ratio is obtained in a known manner through the quotient $(W_w/Y)/(W_d/Y)$. In this way the effect of the material thickness on damping (A) and phase change (F1) is included in the determination of the moisture ratio of the material.

6 Claims, 5 Drawing Figures

METHOD FOR MEASURING THE MOISTURE RATIO OF ORGANIC MATERIAL, AND APPARATUS HEREFOR

The present invention relates to a method for measuring the moisture ratio of organic material, preferably wood, and apparatus herefor.

It is often necessary or desirable in various contexts to determine the moisture ratio of a material, thereby to obtain a measurement of its moisture content.

One such context in which this applies involves the treatment of wood pieces in the so-called sorting department of a saw mill, in which knowledge of the water content of the wood pieces is necessary in order to optimize the preceding drying stage thereof. The invention can also be applied when wishing to measure the moisture ratio of seed and wood chips.

The invention is not limited to any particular field of application, however, but relates to the measurement of the moisture ratio of organic material.

One method of measuring the moisture ratio of organic material is to produce an electric or electromagnetic field therein. The propagation or spread factor of the field is influenced chiefly by the water contained in the material. The water content is normally determined by measuring resistance or capacitance. These values are a measurement of a complex material-constant in the water-bearing material. The material constant is known as the complex, dielectric constant and comprises a true component and an imaginary component $\epsilon'$ and $\epsilon''$, where $\epsilon'$ is the dielectric constant and $\epsilon''$ is a measurement of the loss in the material, and where $\tan \delta = \epsilon''/\epsilon'$.

The moisture ratio is defined as $$m = \frac{W_m - W_d}{W_d} \text{ where}$$

$W_m$ is the weight of the material when wet, and $W_d$ is the weight of the material when dry.

When the density of the material in its dry state is known and is constant, the moisture ratio can be determined simply by measuring the water content. However, the density of many organic materials, such as wood for example, varies. In order to obtain a true value of the moisture content, it is necessary to measure both the water content and the density of the material.

It is also known to determine the water content and density of organic materials with the aid of microwaves. Such a method is found described in the reference Kraszewski, A. "Microwave Aquametry - A review", *Journal of Microwave Power*, 15(4), 1980 p.p. 209-220. It can be said in general that only one transducer is needed when practising such a method. In order to be able to determine two values, namely water content and density, it is necessary to employ two parameters. In this respect there is measured the damping and the phase shift or change of a microwave signal transmitted through the material. These two values are related to the permitivity in accordance with the following relationship:

$$\epsilon' = \left(1 + \frac{F1 \cdot C}{360 \cdot d \cdot f}\right)^2$$

$$\epsilon'' = \frac{\ln A \cdot 2 \cdot C \cdot \sqrt{\epsilon'}}{\omega \cdot d}$$

where f is frequency, $\omega$ is angular velocity, d is thickness, C is the speed of light, A is damping (dB), and F1 is phase shift (degrees).

Damping or attenuation A is a measurement of the water content and the phase shift F1 is a measurement of the density and the water content.

In the aforesaid Kraszewski reference it is given in formula 12 that $A = F_1 (W_w, W_d)$ and that $F1 = F_2 (W_w, W_d)$ where $W_w$ is the weight of the water in the material, $W_d$, and A and F1 have the aforesaid significance, and $F_1$ and $F_2$ represent different functions.

Kraszewski maintains that the moisture ratio can be determined independently of both the density and the thickness of the material. This does not apply in general to the aforesaid formula 12, which describes the model in a general form, but solely when using the special model incorporated in Kraszewski's formula 13, namely $$A = t\left(\frac{W_w}{V} \cdot k_1 + \frac{W_d}{V} \cdot k_2\right) \text{ and}$$

$$F1 = t\left(\frac{W_w}{V} \cdot k_3 + \frac{W_d}{V} \cdot k_4\right) \text{ where}$$

V is the volume of the material and where $k_1$–$k_4$ are constants.

However, it is not possible to measure the moisture ratio of an organic material with the aid of formula 13 without taking density and thickness into account, other than in the case of a material with which the damping (A) as a function of the water content per unit of area ($W_w/Y$) can be described with a single straight line irrespective of thickness, and with which the phase shift or change (F1) as a function of the water content per unit of area ($W_w/Y$) does not vary with thickness. The relationship A as a function of $W_w/Y$ and F1 as a function of $W_w/Y$ respectively is discussed hereinafter.

The problem of measuring with a high degree of accuracy the moisture ratio of organic material whose thickness and/or density varies is solved by the present invention.

Accordingly, the present invention relates to a method for measuring the moisture ratio of material, particularly of organic material, in which microwaves are transmitted to the material whose moisture ratio is to be determined; in which the transmitted microwaves are received subsequent to their transmission through said material; in which the damping (A) of the microwaves and their phase change (F1) upon transmission through the material is determined; and in which the so-called moisture ratio of the material is established with the aid of the determined damping (A) and phase-change values, the method being characterized by determining the term ($W_w/Y$) from the expression $$A = \frac{W_w}{Y} \cdot k_1 + k_3 \cdot t$$

where A is the measured damping and t is the thickness of the material, and where $k_1$ and $k_3$ are constants and are determined by a calibration process, and where the term $W_w/Y$ is the weight of water per unit area; and by determining the term $(W_d/Y)$ from the expression $$F1 = \frac{W_w}{Y} \cdot k_4 + \frac{W_d}{Y} \cdot k_5 + k_6 \cdot t$$

where F1 is the measured phase change, in which expression the aforedetermined term $W_w/Y$ is used, where t is the thickness of the material, the term $W_d/Y$ is the weight of the material in a dry state per unit area, and where $k_4$, $k_5$, $k_6$ are constants and determined by a calibration process; and by deriving the moisture content in a known manner through the ratio $(W_w/Y)/(W_d/Y)$.

The invention also relates to apparatus of the kind set forth in claim 4 and having the characteristic features disclosed therein.

The present invention is based on the understanding that the damping A is influenced by the thickness of the material, rather than the variable $(W_d/Y)$, i.e. the weight of the material in a dry state per unit area, and that in the case of the majority of organic materials the phase change or shift (F1) varies as a function of the water content per unit area $(W_w/Y)$ with the thickness.

By unit area Y above is meant the area perpendicular to the direction of propagation of the microwaves. The terms $(W_w/Y)$ and $(W_s/Y)$ are abbreviated from the respective expressions $$t \cdot \left(\frac{W_w}{y}\right) \text{ and } t \cdot \left(\frac{W_d}{V}\right)$$

where V is the volume of the material and t the thickness thereof.

In several areas where the invention can be applied, no advantage is gained by attempting to eliminate the dependency of the thickness of the material and therewith obtain a less accurate value of the moisture ratio. On the contrary, the thickness of the material is often known. Such is the case in saw mills for example, where a thickness measuring device is often on hand or can be readily installed. By measuring the thickness of the material, or when having knowledge of its thickness, the moisture ratio can be measured with a high degree of accuracy with the aid of the present invention, even in those cases where the density of the material varies. The invention therefore affords a particular advantage when desiring to measure the moisture ratio of wood. The density varies quite considerably between different wood species, such as between pine and spruce.

The present invention will now be described partially with reference to the separate figures of the accompanying drawings, of which FIG. 1 illustrates damping per unit of thickness as a function of the weight of water in the material per unit of volume;

According to the invention the damping A is determined by the relationship $$A = \frac{W_w}{Y} \cdot k_1 + \frac{W_d}{Y} \cdot k_2 + k_3 \cdot t \quad (1)$$

where t is the thickness and $k_1$, $k_2$ and $k_3$ are constants.

In the case of a microwave frequency of say 16 GHz, the constant $k_2$ is so small that the term $W_d/Y \cdot k_2$ can be ignored.

There is then obtained $$A = \frac{W_w}{Y} k_1 + k_3 \cdot t \quad (2)$$

According to the invention the phase change F1 is determined from the relationship $$F1 = \frac{W_w}{Y} \cdot k_4 + \frac{W_d}{Y} \cdot k_5 + k_6 \cdot t \quad (3)$$

where $k_4$, $k_5$, $k_6$ are constants.

Figure 1:
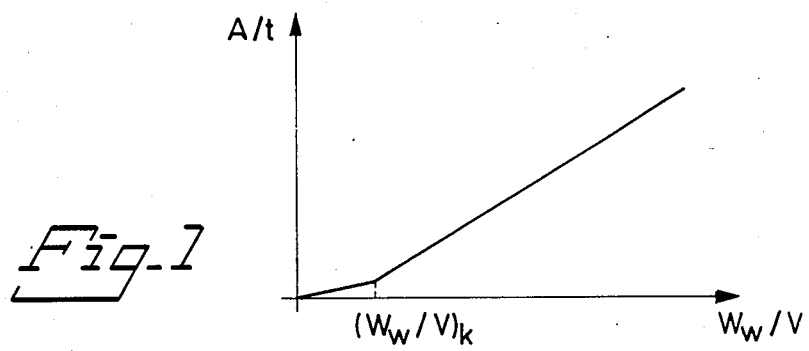

With regard to the relationship (1) above, FIG. 1 shows the principle relationship between damping per unit of thickness A/t and the weight of the water in the material per unit of volume $W_w/V$.

Subsequent to passing a knee, the relationship is approximately linear. The function is approximately independent of the term $W_d/Y$. This non-dependency increases with an increase in microwave frequency. The relationship shown in FIG. 1 illustrates the conditions prevailing at a microwave frequency of 16 GHz. At higher frequencies, up to 20–24 GHz, the dependency on the term $W_d/Y$ is practically zero. The term $W_d/Y$ cannot be ignored at lower frequencies, for example 2450 MHz, where the dependency is greater.

From a general standpoint, the damping or attenuation is affected more precisely by the water contained in the material and the phase change is affected to a still larger extent by the density at higher frequencies. This influence has a maximum at 20–24 GHz.

Consequently, in accordance with a preferred embodiment there is used a microwave frequency above 12 HGz, and beneath 24 GHz, preferably 16 GHz.

Figure 2:
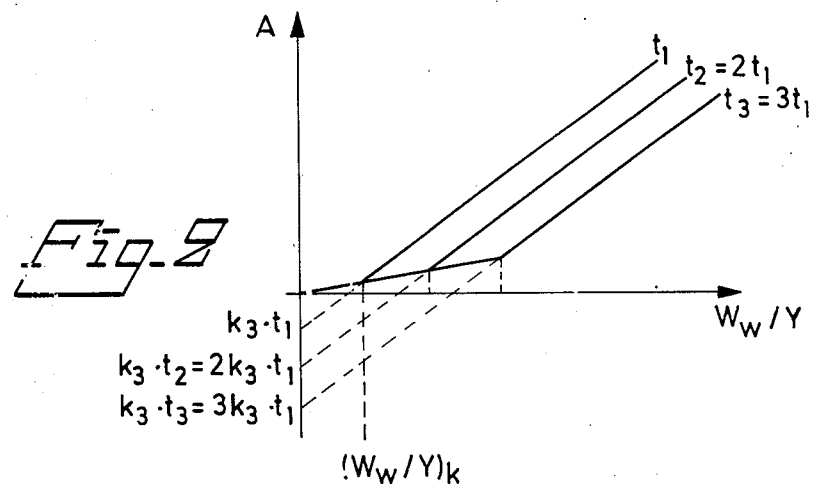
FIG. 2 illustrates damping as a function of the weight of water per unit area in respect of a material of thicknesses $t_1$, $t_2$ and $t_3$ respectively.

FIG. 2 illustrates the relationship between the damping A as a function of the water weight per unit area $(W_w/Y)$ in respect of a material having the thicknesses $t_1$, $t_2$, $t_3$, i.e. the same relationship as that illustrated in FIG. 1 with the variables having been multiplied by t. FIG. 2 shows three curves corresponding to the curve shown in FIG. 1. All curves have a common inclination beneath the respective knees of each curve.

The physical explanation as to why a knee is obtainned at low water concentrations is because the water is bound more firmly to the organic material and does not therewith influence the microwaves to the same extent as the more loosely bound water molecules at higher water concentrations.

The relationship (2) according to the invention derives from the curve to the right of the knee. This section of the curve describes the damping A as a function of the water weight per unit area $W_w/Y$. The knee occurs at very low water concentrations. The knee referenced $(W_w/V)_k$ in FIG. 1 corresponds to the knee $(W_w/Y)_k$ in FIG. 2. According to the relationships in FIGS. 1 and 2

$$\frac{(W_w/Y)_k}{t_1} = (W_w/V)_k \text{ applies at thickness } t_1.$$

Thus, when studying the function in respect of a material piece having the thickness $t_2 = 2t_1$ the following relationship applies:

$$\frac{(W_w/Y)_k}{2t_1} = \frac{1}{2}(W_w/V)_k$$

It will be seen from FIG. 2 that the last term in the relationship (2) describes where respective curves cut the A-axis, i.e. at a value of $k_3 \cdot t_1, 2k_3 \cdot t_1$ and $3 \cdot k_3 \cdot t_1$ respectively.

Thus, the point of intersection with the A-axis depends on the thickness t and not on the term $W_d/Y$. In the aforecited relationship according to Kraszewski $$A = t\left(\frac{W_w}{V} \cdot k_1 + \frac{W_d}{V} \cdot k_2\right) = \frac{W_w}{Y} \cdot k_1 + \frac{W_d}{Y} \cdot k_2$$

it is said instead that damping A depends on $$\frac{W_d}{Y} \text{ and } \frac{W_w}{Y}.$$

In practice, however, there is found a relationship between the dependency of the damping on $W_d/Y$ and on t. The major part of this relationship is proportional. A much better result is obtained when the thickness is used as a variable instead, due to the fact that physically it is the thickness t which influences the damping instead of $W_d/Y$.

Thus, the relationship (2) above is utilized in accordance with the invention in respect of the influence of the damping A. The thickness t is measured and inserted into the relationship or equation, as is also the value of the measured damping A. Thus, the sole unknown term $(W_w/Y)$ can be obtained from the equation (2).

This is inserted in the equation (3) above together with the value of the measured thickness t.

As beforementioned, the invention is also based on the understanding that in the case of the majority of organic materials the phase change or shift (F1) is influenced as a function of the water content per unit area $(W_w/Y)$ with the thickness, in a corresponding manner to that in which the damping (A) is affected. This influence has the same physical basis as that given above.

Figure 3:
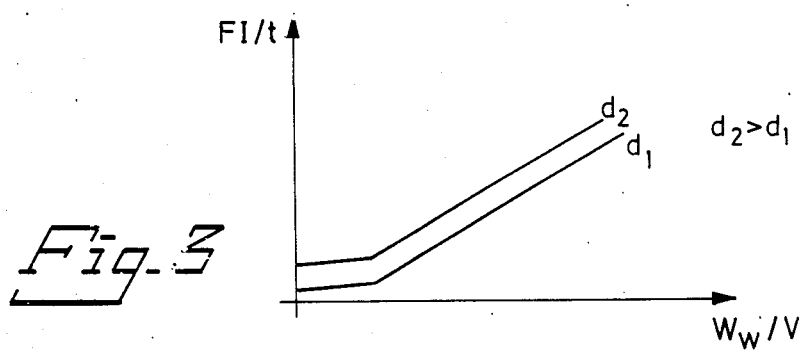
FIG. 3 illustrates the phase change per unit of thickness as a function of the weight of water in the material per unit of volume.

FIG. 3 illustrates the phase change per unit of thickness (F1/t) as a function of the water content per unit volume $(W_w/V)$. As will be seen, each and every one of the curves has approximately the same appearance as the curve in FIG. 1, exhibiting a characteristic knee. It will also be seen that the density of the material affects the function, such that the curve representing the higher density is moved upwards parallel with the lower curve. The density $d_2$ is higher than the density $d_1$.

Figure 4:
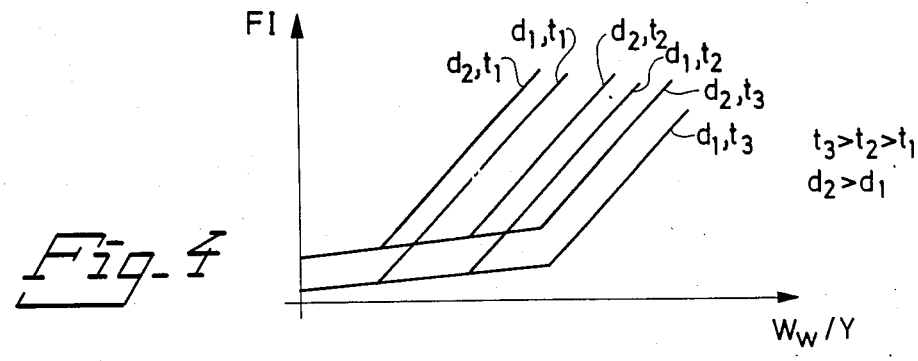
FIG. 4 illustrates the phase change as a function of the weight of water per unit area in respect of a material having thicknesses $t_1$, $t_2$ and $t_3$ and densities $d_1$ and $d_2$.

FIG. 4 illustrates the phase change (F1) as a function of the water content per surface unit $(W_w/Y)$.

As will be seen from FIG. 4, curves corresponding to those illustrated in FIG. 2 are obtained, where a plurality of parallel curves extend from a first inclined curve section. As will be seen from FIG. 3, the position of the first inclined curve section along the F1-axis depends upon the density. Extending from this first curve section are mutually parallel curves whose positions are determined by the thickness t of the material. As will be seen from FIG. 4, the curves are displaced towards a higher value on $W_w/Y$ in respect of a greater thickness, where $t_3 > t_2 > t_1$.

FIG. 4 also indicates that the phase change F1 depends upon the thickness of material of the kind with which the relationship of F1/t to $W_w/V$ exhibits a knee, i.e. at least the majority of organic materials.

The phase change F1 is measured and also inserted into the relationship or equation (3), whereafter the sole unknown term $W_d/Y$ is obtained therefrom.

Because the term $(W_w/Y)$ is determined by taking into account the thickness of the material and is thus far more accurate than would be the case if no attention had been paid to the thickness dependency, the value of the term $W_d/Y$ taken from the relationship (3) affords a higher degree of accuracy.

By also realizing that the phase change or shift F1 is directly affected by the thickness, and therewith inserting the term $k_6 \cdot t$, c.f. the relationship (3), a very accurate result is obtained with respect to the term $W_d/Y$.

Since the density of certain organic materials, such as dry wood, varies considerably between, for example, spruce and pine, it is essential that the term $W_d/Y$ is determined very accurately, since it cannot be considered to be constant when applying the invention in a saw mill for example.

The constants $k_1, k_3, k_4, k_5, k_6$ are determined with the aid of a conventional calibration process.

$$\text{The moisture ratio} = \frac{W_m - W_d}{W_d} = \frac{W_w}{W_d} = \frac{\frac{W_w}{Y}}{\frac{W_d}{Y}}$$

is obtained from the resultant values of the terms $$\frac{W_w}{Y} \text{ and } \frac{W_d}{Y}.$$

Because, as mentioned, the relationship (2) determines the water content as a function of the thickness of the material and the term $(W_w/Y)$ is inserted in the relationship (3), by means of which term $(W_d/Y)$ is determined as a function of the thickness, a correct value of the moisture ratio is obtained even when the thickness and/or density of the material varies.

Because a curve characteristic according to FIGS. 2 and 4 is formed from the common incline for organic material beneath the knee, the present invention can be applied with particular advantage for determining the moisture ratio of organic material where the thickness and/or density thereof varies from case to case or changes within a single piece of material.

A complicating factor when measuring the moisture ratio of organic material is that many organic materials swell, i.e. increase in volume, with increasing water content. Wood is a typical example of such material. In this case, it is preferred to compensate the dependency of the density on the water content.

According to one extremely important embodiment of the invention compensation is made for the dependency of the material density on the water content of said material. In this case the density of the material is measured at the prevailing water content with the aid of the relationship $$\frac{W_{dd}}{Y} = k_7 \cdot \frac{1}{t} \cdot \frac{W_w}{Y} + k_8 \cdot \frac{W_w}{Y} \cdot \frac{W_d}{Y} \quad (4)$$

where the term ($W_{dd}/Y$) is the term ($W_d/Y$) compensated for density variations due to the prevailing water content of the material.

The expression is a second degree polynomial. A relationship $W_{dd} = f(W_w)$ is measured empirically for respective materials, wherewith the constants $k_7$ and $k_8$ are determined.

The values obtained from the relationships (2) and (3) in respect of the terms $$\left(\frac{W_w}{Y}\right) \text{ and } \left(\frac{W_d}{Y}\right)$$

are inserted into the relationship or equation (4).

The moisture ratio is then obtained in a manner analogous with the aforegoing, by utilizing the term $W_{dd}/Y$, i.e.

$$\text{the moisture ratio} = \frac{\frac{W_w}{Y}}{\frac{W_{dd}}{Y}}$$

The moisture ratio thus obtained provides an extremely accurate value of the water content of the material.

It will be evident from the aforegoing that the present invention solves the aforementioned difficulties of measuring the moisture ratio of organic material with a high degree of accuracy, when the thickness and/or the density of the material varies and, in addition, when the density varies with the water content of the material.

Figure 5:
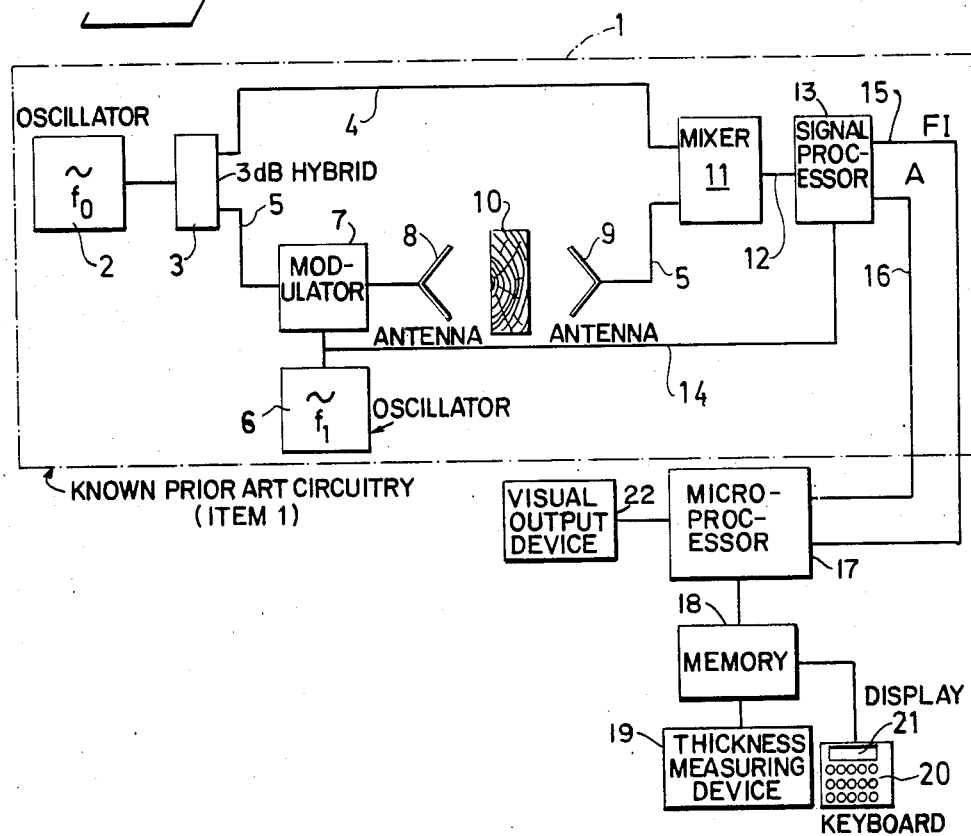
FIG. 5 is a block schematic of apparatus or an arrangement for carrying out the method according to the invention.

FIG. 5 illustrates schematically an arrangement for measuring the moisture ratio of materials, incorporating apparatus according to the present invention.

The arrangement 1 located within the region defined by the chain line is of a known kind and will therefore only be described in brief.

The arrangement 1 includes a microwave oscillator 2 which generates a signal of frequency $f_0$. This signal is passed to a so-called 3 dB-hybrid 3, where the signal is divided between a reference channel 4 and a measuring channel 5. A second oscillator 6 generates a signal of frequency $f_1$, which is substantially lower than the frequency $f_0$.

According to one preferred embodiment of the invention, the frequency $f_0$ exceeds 12 GHz and lies beneath 24 GHz, preferably 16 GHz. The frequency $f_1$ is therefore suitably about 10 KHz. The frequency $f_0$ is modulated in a modulator 7 with the frequency $f_1$, so as to form the frequency $f_0 + f_1$. The signal formed is transmitted by means of a first microwave antenna 8 and is received on a second microwave antenna 9.

The material whose moisture ratio is to be determined, for example a woodpiece 10, is introduced between the pair of antennae 8,9. The signal received in the measuring channel 5 is mixed with the signal in the reference channel 4 in a mixer 11, such as to form a signal having the frequency $f_1$, and is delivered through a conductor 12 to a signal processing circuit 13, to which a signal is also applied directly from the said second oscillator 6, through a conductor 14. The phase change or shift F1 and the damping A are determined in a known manner in the signal processing circuit 13, by comparing the signals on lines 12 and 14 respectively. A signal corresponding to the phase change F1 and a signal corresponding to the damping A is formed on the outputs 15,16 of the signal processing circuit.

In accordance with the present invention, the signals F1 and A respectively are passed through respective conductors 15 and 16 to a calculating unit which incorporates a microprocessor 17 or the like. The microprocessor 17 incorporates a memory 18, which suitably comprises a RAM-memory or the like. There is also provided a suitable means 19 of known kind for measuring the thickness of the material piece 10 whose moisture ratio is to be determined and/or an infeed unit 20, such as keyboard or the like, for feeding in the thickness of the material piece 10, this thickness being determined in some other way or being known. The keyboard 20 may be provided with a display 21 on which the thickness fed into the microprocessor is displayed.

The means 19 and the infeed unit 20 are connected to the memory 18 in which the pertinent thickness is stored.

According to the present invention the computer unit is adapted to calculate the value of the term ($W_w/Y$) in the expression $$A = \left(\frac{W_w}{Y}\right) \cdot k_1 + k_3 \cdot t$$

where A is the damping obtained on the conductor 16 and t is the thickness of the material obtained from the memory 18, and where $k_1$ and $k_3$ are constants, which are also found stored in the memory 18. The constants $k_1$ and $k_3$ are determined by a suitable conventional calibration process, whereafter the values obtained are introduced into the memory. The computer unit introduces the value of the term ($W_w/Y$) into the memory 18.

The computer unit 17 is also adapted to calculate the value of the term ($W_d/Y$) in the expression $$F1 = \frac{W_w}{Y} \cdot k_4 + \frac{W_d}{Y} \cdot k_5 + k_6 \cdot t$$

where F1 is the phase change or shift obtained from the conductor 15 and t is the thickness of the material. In this case, the computer unit is adapted to collect the value of the term ($W_w/Y$) from the memory and insert said value into the expression for F1. The constants $k_4$, $k_5$, $k_6$ are determined by a suitable conventional calibration process, whereafter the values obtained are introduced into the memory.

The constants, $k_1$, $k_3$, $k_4$, $k_5$ and $k_6$ are determined prior to commencing the measuring process in question.

The computer unit 17 is adapted to then form the moisture ratio, by carrying out the calculation ($W_w/Y$)/($W_d/Y$).

In accordance with one preferred embodiment of the invention, which can be applied to advantage when the material whose moisture ratio is to be determined has properties such that its density is a function of its water content, the computer unit is adapted, subsequent to determining the value of the terms ($W_w/Y$) and ($W_d/Y$)

respectively to calculate the value of the term $(W_{dd}/Y)$ from the expression $$(W_{dd}/Y) = k_7 \left(\frac{W_w}{Y}\right)^2 + k_8 \cdot \frac{W_w}{Y} + \frac{W_d}{Y}$$

while utilizing the value of the terms $(W_w/Y)$ and $(W_d/Y)$, where the term $(W_{dd}/Y)$ is the term $(W_d/Y)$ compensated for density variations due to the prevailing water content of the material. The constants $k_7$ and $k_8$ are also determined by means of a suitable conventional calibration process and introduced into the memory 18. This calibration process thus includes an empirical determination of the aforesaid expression in respect of a pertinent material.

The computer unit 17 is adapted to then form the moisture ratio, by making the calculation $(W_w/Y)/(W_{dd}/Y)$.

The value of the moisture quotient $(W_w/Y)/(W_d/Y)$ or, when applicable, $(W_w/Y)/(W_{dd}/Y)$ is fed to a suitable visualizing device 22, such as a display unit, a writer, lamps or the like.

It will be understood that the block schematic illustrated in FIG. 5 and associated descriptive text, particularly with reference to the arrangement located within the region defined by chain lines, shall be considered an embodiment where the invention is applied. Any other array of apparatus or devices for calculating phase change and damping can be used together with the present invention.

Instead of the arrangement illustrated in the region defined by said chain lines, there can be used to advantage an arrangement described in the Swedish patent application No. 8403438-8.

Thus, the invention shall not be considered to be restricted to the aforedescribed embodiments and it will be understood that modifications can be made within the scope of the following claims.

I claim:

1. A method of measuring the moisture ratio of material, particularly organic material, comprising: measuring the thickness of the material for which the moisture ratio is to be measured, transmitting microwaves to and through the thickness dimension of the material whose moisture ratio is to be determined and receiving the transmitted microwaves subsequent to their transmission through said material; measuring the damping (A) and phase change (F1) of the microwaves upon their transmission through the material and calculating the so-called moisture ratio of the material on the basis of the measured damping (A) and phase change, and determining the term $(W_w/Y)$ from the expression $$A = \frac{W_w}{Y} \cdot k_1 + k_3 \cdot t$$

where A is the measured damping value and t is the thickness of the material, where $k_1$ and $k_3$ are constants determined by a calibration process, and where the term $W_w/Y$ is the weight of the water in the material per unit area; by determining the term $(W_d/Y)$ from the expression $$F1 = \frac{W_w}{Y} \cdot k_4 + \frac{W_d}{Y} \cdot k_5 + k_6 \cdot t$$

where F1 is the measured phase change, in which expression the aforedetermined term $W_w/Y$ is utilized, where t is the thickness of the material, where the term $W_d/Y$ is the weight of the material in a dry state per unit area, and where $k_4$, $k_5$, $k_6$ are constants determined by a calibration process; and by forming the moisture ratio in a known manner from the ratio $(W_w/Y)/(W_d/Y)$.

2. A method according to claim 1, characterized by a further step of determining the term $(W_{dd}/Y)$ from the expression $$(W_{dd}/Y) = k_7 \cdot \frac{1}{t} \cdot \left(\frac{W_w}{Y}\right)^2 + k_8 \cdot \frac{W_w}{Y} + \frac{W_d}{Y}$$

where the term $(W_{dd}/Y)$ is the term $(W_d/Y)$ compensated for density variations due to the prevailing water content of the material, and where $k_7$ and $k_8$ are constants determined by a calibration process; and by forming the moisture ratio from the quotient of $(W_w/Y)/(W_{dd}/Y)$.

3. A method according to claim 1 or 2, characterized by using a microwave frequency exceeding 12 GHz and beneath 24 GHz, preferably a frequency of 16 GHz.

4. Apparatus for measuring the moisture ratio of material, particularly organic material, comprising: means for measuring the thickness of the material, microwave oscillators (2,6), a modulator (7), a pair of spaced-apart antennae (8,9) between which the material (10) in question is intended to be placed with its measured thickness dimension aligned with the path between said antennae, a mixer (11), and a signal processing circuit (13), said circuit being adapted to product two signals (A) and (F1) which correspond respectively to the damping (A) and the phase change (F1) of the microwaves upon transmission thereof through the material (10), and a computer unit (17) for calculating the so-called moisture ratio of the material, wherein the computer unit (17) is adapted to calculate from the measured value of the damping (A) and from the measured value of the thickness (t) of the material fed into a memory (18) associated with the computer unit (17) the value of the term $(W_w/Y)$ from the expression $$A = \left(\frac{W_w}{Y}\right) \cdot k_1 + k_3 \cdot t,$$

where the term $(W_w/Y)$ is the weight of water in the material per unit area, and is adapted to then calculate from the measured value of the phase change (F1) and from said thickness (t) and the calculated value of the term $(W_w/Y)$ the value of the term $(W_d/Y)$ from the expression $$F1 = \frac{W_w}{Y} \cdot k_4 + \frac{W_d}{Y} \cdot k_5 + k_6 \cdot t$$

where the term $W_d/Y$ is the weight of the material in a dry state per unit area and where said constants $k_1$, $k_3$, $k_4$, $k_5$ and $k_6$ are determined by a calibration process and fed into the memory (18), and adapted to form the moisture ratio by carrying out the calculation $(W_w/Y)/(W_d/Y)$.

5. Apparatus according to claim 4, characterized in that the computer unit is adapted, subsequent to having calculated the value of the terms $(W_w/Y)$ and $(W_d/Y)$ respectively, to calculate the value of the term $(W_{dd}/Y)$ from the expression $$(W_{dd}/Y) = k_7 \cdot \left(\frac{W_w}{Y}\right)^2 + k_8 \left(\frac{W_w}{Y}\right) + \left(\frac{W_d}{Y}\right)$$

where the term $(W_{dd}/Y)$ is the term $(W_d/Y)$ compensated for density variations due to the prevailing water content of the material (10), and where the constants $k_7$ and $k_8$ are determined by a calibration process and fed into the memory (18), and adapted to form the moisture ratio by carrying out the calculation $(W_w/Y)/(W_{dd}/Y)$.

6. Apparatus according to claim 4 or 5, characterized in that one of said oscillators is adapted to generate a frequency exceeding 12 GHz and beneath 24 GHz, preferably 16 GHz.

* * * * *

UNITED STATES PATENT AND TRADEMARK OFFICE
CERTIFICATE OF CORRECTION

PATENT NO. : 4,675,595
DATED : June 23, 1987
INVENTOR(S) : BENGT HANE

It is certified that error appears in the above-identified patent and that said Letters Patent is hereby corrected as shown below:

On the cover sheet, in the Assignee's name (item 73), change "Stiftesen" to --Stiftelsen--.

In the specification (claim 4):

Column 10, line 38, change "product" to --produce--.

Signed and Sealed this

First Day of December, 1987

Attest:

DONALD J. QUIGG

*Attesting Officer*   *Commissioner of Patents and Trademarks*